United States Patent [19]

Tsuji et al.

[11] Patent Number: 4,701,536

[45] Date of Patent: Oct. 20, 1987

[54] NOVEL 10-MEMBERED RING COMPOUND AND PROCESS FOR PREPARING THE SAME

[75] Inventors: Jiro Tsuji, Kamakura; Takashi Takahashi, Tokyo, both of Japan

[73] Assignee: UBE Industries, Ltd., Ube, Japan

[21] Appl. No.: 882,592

[22] Filed: Jul. 7, 1986

[30] Foreign Application Priority Data

Jul. 10, 1985 [JP] Japan .................................. 60-150091

[51] Int. Cl.[4] ...................... C07D 303/02; C07F 7/02; C07F 7/08; C07F 7/18
[52] U.S. Cl. .................... 549/215; 556/436; 549/13; 549/28; 549/414; 549/416; 549/546; 568/329; 568/375
[58] Field of Search ................ 556/436; 549/215, 546, 549/416, 13, 28, 414; 568/329, 375

[56] References Cited

U.S. PATENT DOCUMENTS

| | | | |
|---|---|---|---|
| 2,544,737 | 3/1951 | Theobald | 568/375 X |
| 3,786,099 | 1/1974 | Howell et al. | 568/375 X |
| 4,268,445 | 5/1981 | Kropp et al. | 568/375 X |

FOREIGN PATENT DOCUMENTS 55-2265  2/1980  Japan ................... 549/546
59-16848  1/1984  Japan ................... 568/375

Primary Examiner—Paul F. Shaver
Attorney, Agent, or Firm—Frishauf, Holtz, Goodman & Woodward

[57] ABSTRACT

Disclosed are a compound of Formula I:

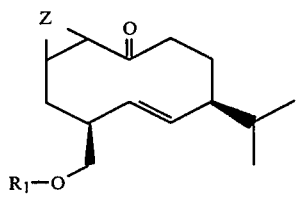

wherein $R_1$ represents a hydrogen atom or a protective group for a hydroxyl group; and Z represents a direct bond (2,3-cis-5R*, 8S*) or an oxygen atom which forms an oxirane ring having a configuration of (2R*, 3R*, 5R*, 8S*), and a process for preparing the same.

By use of the above compound as an intermediate, there can be synthesized periplanone-B which is a sex pheromone of periplaneta.

8 Claims, No Drawings

NOVEL 10-MEMBERED RING COMPOUND AND PROCESS FOR PREPARING THE SAME

BACKGROUND OF THE INVENTION

The present invention relates to a novel 10-membered ring compound and a process for preparing the same, and more specifically to an intermediate for synthesis of periplanone-B which is a sex pheromone of a periplaneta and a process for preparing the same.

The sex pheromone of periplaneta was isolated in an amount of 28 μg from uncopulated female periplanetas and found to attract male periplanetas in a trace amount of $10^{-5}$ pg by Wharton et al in 1962 [Science, 137, 1062]. Since the pheromone exists in nature in an extremely small amount, the determination of its structure was not done for a long time. However, in 1976, 200 μg of periplanone-B were isolated from 75,000 uncopulated female periplanetas and the structure of the periplanone-B was analized by Persoons et al to propose a chemical structure having a ten-membered ring therefor [Tetrahedron Lett. 2055]. In 1979, Still et al succeeded in a total synthesis of an active form of periplanone-B according to chemical synthesis methods [J. Am. Chem. Soc.; 101, 2495], thereby the stereostructure of periplanone-B was clarified. Still et al filed a patent application based on this synthesis (U.S. Pat. No. 4,339,338).

Thereafter, in 1984, Schreiber et al disclosed a synthesis of periplanone-B by use of an photochemical reaction [J. Am. Chem. Soc.; 106, 4038].

According to the method of Still et al, a reaction must be proceeded with retaining the stereo-structure, by using a substituted cyclohexenone as a starting material, whereas the starting material 5-hydroxymethyl-2-cyclohexenone, which is synthesized from 3,5-dihydroxy benzoic acid through three steps [J. Am. Chem. Soc.; 75, 4405, (1956)], is too expensive for a starting material. Further, the reaction to synthesize a 10-membered ring, by use of an oxy-Cope rearrangement reaction, from a cyclohexenol intermediate gives a yield of as low as 57%.

On the other hand, in the synthetic method of Schreiber et al, 4-isopropyl-2-cyclohexen-1-one and allene, both of which are expensive, are employed, and also an photochemical reaction device is required for the condensation reaction thereof. In addition, in the above two inventions, in the epoxydation process, stereo selectivity to the desired specific stereoisomer is as low as 80%.

SUMMARY OF THE INVENTION

An initial object of the present invention is to overcome the problems in producing periplanone-B which is a sex pheromone of periplaneta, and further object is to provide a process for preparing periplanone-B in high yield using inexpensive materials without any consideration of the stereo-structure of the starting materials as well as to provide a novel 10-membered ring compound which is useful as materials for synthesis.

Namely, the present invention relates to a novel 10-membered ring compound represented by Formula I:

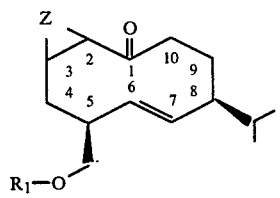

wherein $R_1$ represents a hydrogen atom or a protective group for a hydroxyl group; and Z represents a direct bond (2,3-cis-5R*, 8S*) or an oxygen atom which forms an oxirane ring having a configuration of (2R*, 3R*, 5R*, 8S*).

The present invention also relates to a process for producing the above novel 10-membered ring compound, which comprises reacting a compound of Formula II:

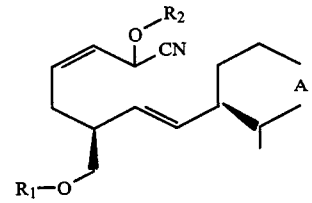

wherein $R_1$ represents a hydrogen atom or a protective group for a hydroxyl group; $R_2$ represents a protective group for a hydroxyl group in α-cyanohydrin; and A represents a group capable of being eliminated, with a base, followed by treatment with an acid and subsequently with a base to obtain a compound of Formula III:

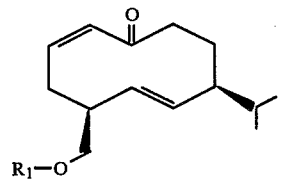

wherein $R_1$ has the same meanings as defined above and further directly epoxydizing site-specifically and stereo-specifically the double bond at α- and β-positions relative to the carbonyl group of the thus obatained compound of the above Formula III, in either case where $R_1$ of said compound represents a protective group for hydroxyl group or a hydrogen atom, to obtain a compound of Formula IV:

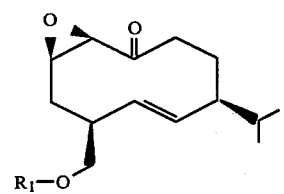

wherein $R_1$ has the same meanings as defined above, and hydrolyzing the thus obtained compound of the above Formula IV when $R_1$ represents a protective group for a hydroxyl group to obtain a compound of Formula IV':

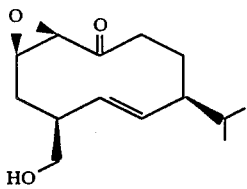

IV'

DETAILED DESCRIPTION OF THE PREFERRED EMBODIMENTS

First of all, the novel 10-membered ring compound, which is the first invention of the present invention, will be described in detail.

Although the protective group for a hydroxyl group represented by $R_1$ in the novel compound of Formula I according to the present invention may be of any kind, it may preferably be a $$X_2 - \underset{\underset{X_3}{|}}{\overset{\overset{X_1}{|}}{Si}} - \text{group}$$

wherein $X_1$, $X_2$ and $X_3$ may be the same or different and each represent a lower alkyl group having 1 to 4 carbon atoms such as methyl, ethyl, n-propyl, isopropyl, n-butyl, isobutyl, sec-butyl, tert-butyl, etc., an arylalkyl group such as a substituted or unsubstituted benzyl group, etc., or an aryl group such as a phenyl group, etc.;
a tetrahydropyranyl group, a tetrahydrothiopyranyl group, a benzyloxymethyl group, an ethoxyethyl group or a methoxymethyl group, more preferably a

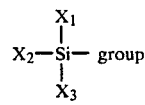

wherein $X_1$, $X_2$, and $X_3$ each have the same meanings as defined above.

Typical examples of the present novel compound may be, for example, 8-isopropyl-5-(t-butyldiphenyl-siloxy)methyl-2,6-cyclodecadien-1-one, 8-isopropyl-5-(trimethylsiloxy)methyl-2,6-cyclodecadien-1-one, 8-isopropyl-5-(dimethyl-t-butylsiloxy)methyl-2,6-cyclodecadien-1-one, 8-isopropyl-5-(triphenylsiloxy)-methyl-2,6-cyclodecadien-1-one, 8-isopropyl-5-(diphenylmethylsiloxy)methyl-2,6-cyclodecadien-1-one, 8-isopropyl-5-(1-ethoxyethoxy)-methyl-2,6-cyclodecadien-1-one, 8-isopropyl-5-(2-ethoxy-2-propoxy)methyl-2,6-cyclodecadien-1-one, 8-isopropyl-5-(tetrahydropyranyl-oxy)methyl-2,6-cyclodecadien-1-one, 8-isopropyl-5-(t-butoxy)methyl-2,6-cyclodecadien-1-one, 8-isopropyl-5-(benzyloxymethoxy)methyl-2,6-cyclodecadien-1-one, 8-isopropyl-5-(t-butyldiphenylsiloxy)methyl-2,3-epoxy-6-cyclodecen-1-one, 8-isopropyl-5-(trimethylsiloxy)methyl-2,3-epoxy-6-cyclodecen-1-one, 8-isopropyl-5-(dimethyl-t-butylsiloxy)methyl-2,3-epoxy-6-cyclodecen-1-one, 8-isopropyl-5-(triphenylsiloxy)methyl-2,3-epoxy-6-cyclodecen-1-one, 8-isopropyl-5-(diphenylmethylsiloxy)methyl-2,3-epoxy-6-cyclodecen-1-one, 8-isopropyl-5-(1-ethoxyethoxy)-methyl-2,3-epoxy-6-cyclodecen-1-one, 8-isopropyl-5-(2-ethoxy-2-propoxy)methyl-2,3-epoxy-6-cyclodecen-1-one, 8-isopropyl-5-(tetrahydropyranyloxy)methyl-2,3-epoxy-6-cyclodecen-1-one, 8-isopropyl-5-(t-butoxy)methyl-2,3-epoxy-6-cyclodecen-1-one, 8-isopropyl-5-(benzyloxymethoxy)methyl-2,3-epoxy-6-cyclodecen-1-one, 8-isopropyl-5-hydroxymethyl-2,3-epoxy-6-cyclodecen-1-one.

Next, the preparation method of the above novel compound, which is the second invention of the present invention, will be illustrated.

The preparation method according to the present invention may be shown by the following synthesis route:

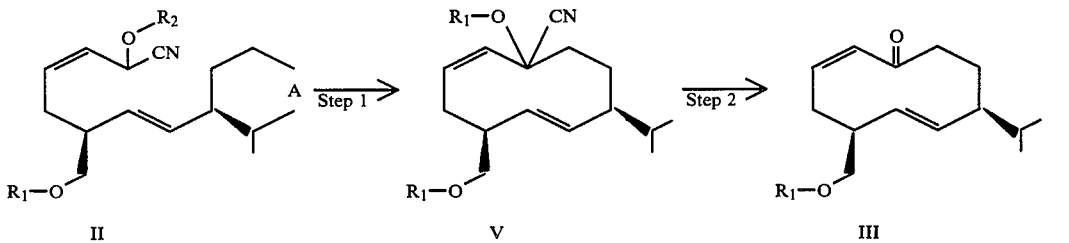

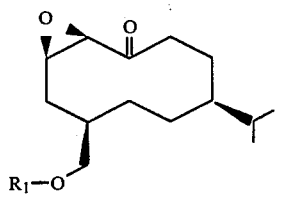 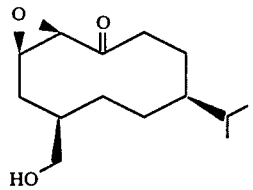

IV → Step 4 → IV'

[wherein $R_1$ represents a protective group for a hydroxyl group]

First, description will be made on Step 1 and Step 2.

A compound of Formula II, wherein $R_1$ has the same meaning as defined above; $R_2$ represents a hydrogen atom or a protective group for α-cyanohydrin, preferably one selected from the group consisting of a lower alkoxyalkyl group such as methoxymethyl, ethoxyethyl, ethoxymethyl, etc., a silyl group substituted by a lower alkyl group having 1 to 3 carbon atoms such as methyl, ethyl, propyl, etc., a benzyloxymethyl group, a tetrahydropyranyl group and a substituted or unsubstituted benzoyl group; and A represents a group capable of being eliminated, preferably a halogen atom or —O—$R_3$, wherein $R_3$ represents a lower alkyl group such as methyl, ethyl, etc., a benzenesulfonyl group unsubstituted or substituted with a halogen atom or a nitro group, a lower alkylsulfonyl group unsubstituted or substituted by a fluorine atom, a nitrobenzoyl group, etc, more preferably a benzenesulfonyl group or a p-toluenesulfonyl group, is reacted with a base. In the above reaction, it is desirable to select a suitable base taking into consideration the acidity of the active proton at the α-position of cyanohydrin II, steric bulkiness of $R_2$, eliminability of A, etc., and there may preferably be used lithium bis(trimethylsilyl)amide, lithium diisopropylamide, lithium-t-butoxide, sodium hydride, sodium amide, potassium hydride or potassium amide, most preferably lithium bis(trimethylsilyl)amide. As a solvent for the reaction, there may be preferably employed an aromatic hydrocarbon such as benzene, toluene, etc., tetrahydrofuran, dioxane, ether, etc., and most preferably benzene or tetrahydrofuran. Reaction temperature may preferably be from 0° to 150° C., most preferably from room temperature to 100° C. Reaction time may preferably be from 10 minutes to 3 hours, most preferably from 30 minutes to 1.5 hours. It is desired to conduct this reaction in nitrogen or argon stream. The resulting product may be purified by silica gel chromatography and others. However, it may be used as such without purification for the subsequent reaction.

As the acid to produce the compound III from the compound V, hydrochloric acid, acetic acid, p-toluenesulfonic acid, benzenesulfonic acid, sulfonic acid, pyridinium p-toluenesulfonate or an acidic ion exchange resin are preferred, and most preferably p-toluenesulfonic acid, benzene sulfonic acid or pyridinium p-toluenesulfonate may be employed. As the solvent for the reaction, a lower alcohol such as methanol, ethanol, etc. is preferred, and most preferably methanol or ethanol may be employed. Reaction temperature may preferably be from −10° C. to room temperature, most preferably from 0° C. to room temperature. Reaction time may usually be from 10 minutes to 3 hours, preferably from 30 minutes to 1.5 hours. Then, base treatment is conducted at 0° C. to room temperature and such a base treatment may preferably be conducted by stirring the reaction mixture in an aqueous alkali (e.g. potassium carbonate, potassium hydroxide, sodium carbonate, sodium hydroxide, sodium hydrogen carbonate, etc.) solution for 5 to 30 minutes or by using a basic ion exchange resin instead of the alkali. After treatment, the reaction mixture is extracted with ether, etc.

Subsequently, the resulting reaction mixture is purified through chromatography [as a carrier silica gel etc. is preferred; as an eluent, ether, benzene, hexane, chroloform, ethyl acetate, etc. are preferred; and a mixed solvent of ether-hexane (1:5 to 1:20) is most preferred] to obtain a compound of formula III.

Next, description will be made on Step 3.

The compound of Formula III, wherein $R'_1$ has the same meanings as defined for the above $R_1$ except for hydrogen atom, is reacted with a peroxide, preferably t-butyl hydroperoxide, peracetic acid, hydrogen peroxide, m-chlorobenzoic acid, perbenzoic acid, p-nitroperbenzoic acid or monoperoxyphthalic acid and a base, preferably potassium hydride, sodium hydride, N-benzyltrimethylammonium hydroxide, triethylamine or diisopropylethylamine at a temperature from −78° to 50° C., preferably from −10° C. to room temperature to epoxydize site-specifically and stereo-specifically the double bond at α- and β-positions relative to the carbonyl group thereof. By the above reaction there can be obtained the compound of Formula IV when $R_1$ is a protective group for a hydroxyl group or a compound of Formula IV' when $R_1$ is a hydrogen atom.

Further, the compound of Formula IV can be converted, according to Step 4, to 8-isopropyl-5-hydroxymethyl-2,3-epoxy-6-cyclodecen-1-one of Formula IV' through hydrolysis in the presence of an acid (e.g. 1 wt.% hydrochloric solution, 50 wt.% acetic acid solution or methanolic p-toluenesulfonic acid), a base (e.g. 10% NaOH, 10% KOH or aqueous ammonia) or a salt (e.g. tetrabutylammonium fluoride, cesium fluoride or potassium fluoride) at a temperature from −40° to 50° C., preferably from −10° C. to room temperature.

The compound of formula II which is an essential starting material for the first and second inventions of the present invention can be prepared, for example, through a synthesis route of the following schemes:

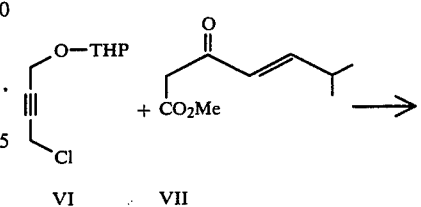

VI   VII

-continued

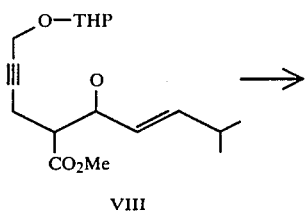
VIII

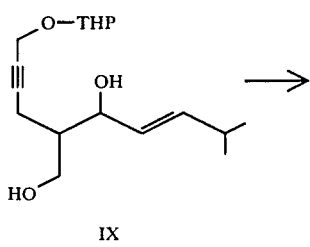
IX

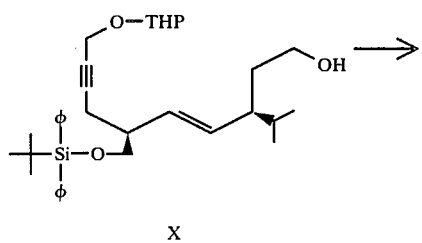
X

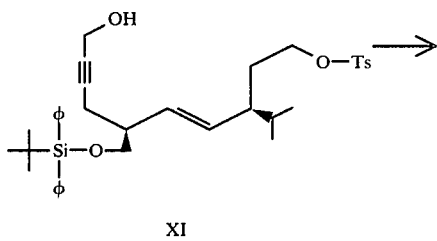
XI

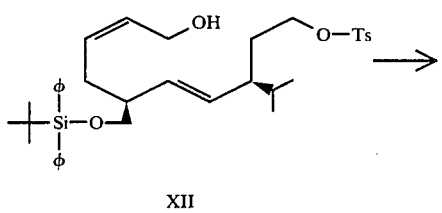
XII

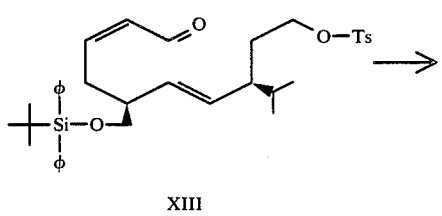
XIII

-continued

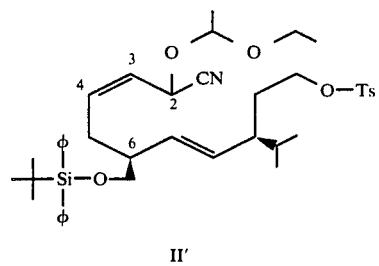
II'

In the above schemes, THP represents a tetrahydropyranyl group, Me represents a methyl group, $\phi$ represents a phenyl group ―― represents a t-butyl group and Ts represents a tosyl group.

First, a compound of Formula VI can be prepared from 2-butyne-1,4-diol according to a conventional procedure. A compound of the formula VII can also be prepared from the reaction between an inexpensive acetalated isobutylaldehyde and a diketene.

The compounds of Formula VI and Formula VII are condensed with a base to form a compound of Formula VIII. The Compound VIII is converted to Compound IX by reducing the carbonyl moiety with L-selectride LiB[CH(CH$_3$)C$_2$H$_5$]$_3$H, subsequently the ester moiety with lithium aluminum hydride. After the hydroxyl group at the methyl-hydroxy moiety of Compound IX is protected with a protective group, the resulting compound is reacted with methylorthoacetate in the presence of a catalytic amount of n-heptoic acid, followed by reduction of the ester moiety to form Compound X. The hydroxyl group of the Compound X is tosylated through reaction with p-toluenesulfonyl chloride and then tetrahydropyran (THP) is eliminated using p-toluenesulfonic acid in methanol to form Compound XI. The Compound XI is subjected to catalytic hydrogenation with a Lindlar catalyst (Pd/CaCO$_3$) to form Compound XII. The Compound XII is oxidized with manganese dioxide to form Compound XIII. The Compound XIII is reacted with trimethylsilyl cyanide and 18-crown-6/KCN, subsequently with benzyltrimethylammonium fluoride, and finally with ethyl vinyl ether in the presence of a catalytic amount of p-toluenesulfonic acid to obtain a compound of Formula II'.

The compound of the first invention according to the present invention may be utilized for the synthesis of periplanone-B which is a sex pheromone of periplaneta, for example, as shown in the synthesis route of the following scheme:

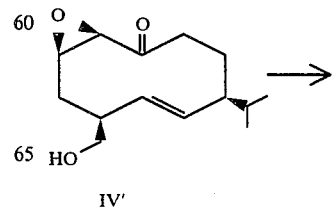
IV'

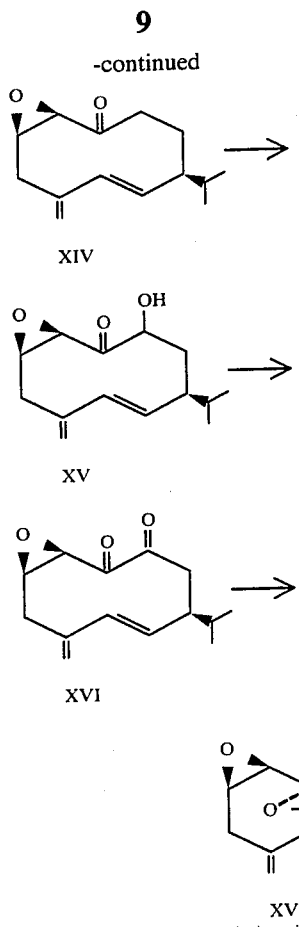

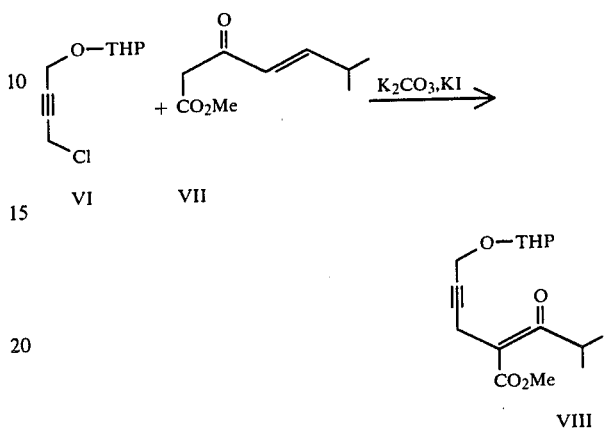

PREPARATION EXAMPLE 1

Preparation of methyl 6-methyl-3-oxo-2-(4-tetrahydropyranyloxy-2-butinyl)-(E)-4-heptenoate (Compound VIII)

Namely, the Compound IV' is reacted with o-nitrophenylselenonitrile and tributylphosphine, subsequently with hydrogen peroxide to obtain Compound XIV. Then, Compound XIV is reacted with lithium bis(trimethylsilyl)amide in the presence of hexamethylphosphoramide (HMPA) in nitrogen stream, followed by addition of triethylphosphite and introduction of oxygen to obtain Compound XV. The Compound SV is reacted with pyridinium chlorocromate (PCC) to obtain Compound XVI. The compound XVI is finally reacted with sodium hydride and trimethylsulfonium iodide in dimethylsulfoxide to yield (±) periplanone-B of Formula XVII.

compounds XIV and XVI are known compounds [J. Am. Chem. Soc.; 106, 4038, (1984)].

Periplanone-B is very important in a biological phenomenon, i.e., reproduction in periplaneta, and plays a significant role as a chemical factor in a series of processes that periplanone-B, included in the body of a female periplaneta, attracts a male periplaneta, so that the male can find the female and acknowledge that it is a female of the same kind, leading to combination of the couplatory organs. Accordingly, the present invention, providing a process which facilitate synthesis of such a compound is extremely useful not only in academic fields but also in industries and in its turn for human beings in their social life.

Hereinafter, Preparation examples of the starting material and Examples, and Referential examples in the case where applied to total synthesis of periplanone-B of the present invention will be specifically described.

To acetone (50 ml) were added propargyl chloride IV (1.25 g, 6.6 mmol), β-ketoester VII (1.88 g, 11.1 mmol), potassium carbonate (1.55 g, 11.7 mmol) and potassium iodide (2.4 g, 14 mmol), followed by reflux under heating for 4 hours. After cooling, the reaction mixture was poured into diluted hydrochloric acid, followed by extraction with ether. The organic layer was washed with a saturated sodium bicarbonate solution, washed with a saturated brine and dried over magnesium sulfate. The solvent was removed by evaporation under reduced pressure, the residue was further subjected to distillation under reduced pressure to remove excess of Compound VII. A brown oil remained was purified through silica gel column chromatography to give a product of 1.7 g of compound VIII (yield 80%). The compound thus obtained indicated the physicochemical properties shown below and was identified as the title compound.

IR (neat); 2920, 2840, 1760, 1720, 1630, 1440, 1360, 1120, 970, 900, 880 cm$^{-1}$.

$^1$H NMR (CDCl$_3$) δ ppm: 6.95 (dd, 1H, J=6.4, 15.4 Hz,) 6.20 (d, 1H, J=15.4 Hz,) 4.75 (wide s, 1H,) 4.16 (wide s, 2H,) 3.96 (t, 1H, J=7.7 Hz,) 3.70 (s, 3H,) 3.3–3.8 (m, 3H,) 2.9–2.3 (m, 3H,) 1.8–1.3 (m, 6H,) 1.09 (d, 6H, J=6.4 Hz,).

PREPARATION EXAMPLE 2

Preparation of 6-methyl-2R*-(4-tetrahydropyranyloxy-2-butinyl)-(E)-4-heptene-1,3R*-diol (Compound IX)

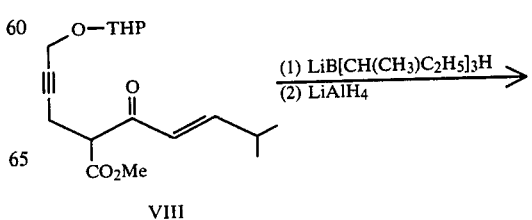

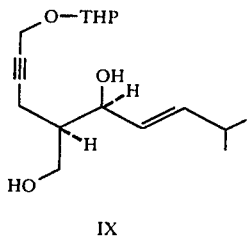

L-Selectoride (22 ml, 22 mmol, 1M solution/THF) was added gradually at −78° C. to a tetrahydrofuran solution of β-ketoester VIII (4.7 g, 14.7 mmol). The resulting mixture was stirred at −78° C. for 1 hour, and then was poured into an aqueous 3-N hydrochloric acid, followed by extraction with ether. The organic layer was washed with a saturated aqueous sodium bicarbonate solution, washed with a saturated brine and dried over magnesium sulfate. The solvent was removed by evaporation to obtain an oily substance. The oily substance was dissolved in 10 ml of ether, followed by dropwise addition at 0° C. to a suspension of lithium aluminum hydride (560 mg, 14.7 mmol) in ether (50 ml). After the resulting mixture was stirred for 30 minutes, a small amount of 2% aqueous sodium hydroxide solution was gradually added thereto. After filtration, the organic layer was concentrated and the oily substance was purified through silica gel column chromatography to give 2.4 g (yield 56%) of diol IX. The compound thus obtained indicated the physicochemical properties as shown below and therefore it was identified as the title compound.

IR (neat); 3360 (br), 2910, 2210, 1440, 1350, 1200, 1020, 900, 870, 810, 730 cm$^{-1}$.

$^1$H NMR (CDCl$_3$) β ppm: 5.65 (dd, J=5.4, 15.4 Hz, 1H,) 5.40 (dd, J=6.4, 15.4 Hz, 1H,) 4.75 (wide s, 1H,) 4.18 (wide s, 2H,) 3.24–4.05 (m, 5H,) 2.1–2.5 (m, 3H,) 1.4–1.9 (m, 7H,) 1.03 (d, J=6.7 Hz, 6H,).

PREPARATION EXAMPLE 3

Preparation of 6R*-(t-butyldiphenylsiloxy)methyl-3S*-isopropyl-10-tetrahydropyranyloxy-(E)-4-decen-8-in-1-ol (Compound X)

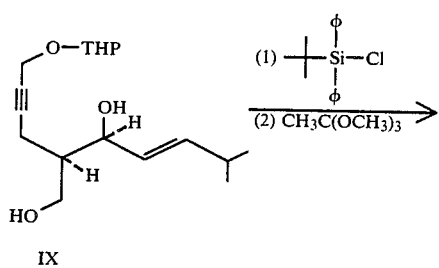

The diol IX (3.6 g, 12.6 mmol), triethylamine (1.9 ml, 13.9 mmol) and dimethylaminopyridine (61 mg, 0.5 mmol) were dissolved in dichloromethane (50 ml), and to the resulting solution was added dropwise at 0° C. t-butylchlorodiphenylsilane (3.6 ml, 13.9 mmol) in nitrogen stream. After stirring for 20 minutes, the reaction mixture was poured into an aqueous 1N-hydrochloric acid, followed by extraction with ether. The organic layer was washed with a saturated sodium bicarbonate solution, washed with a saturated brine and dried over magnesium sulfate. The solvent was removed by evaporation under reduced pressure and an oily substance was purified through silica gel column chromatography to give 3 g of a mono-t-butyldiphenylsilyl derivative. The thus obtained compound was dissolved together with trimethyl orthoacetate (2.06 g, 17 mol) and a catalytic amount of n-heptoic acid in xylene (10 ml), and the resulting solution was heated at 140° C. for 1 hour while removing methanol. The reaction solution was cooled to room temperature, poured into a saturated aqueous sodium bicarbonate solution and extracted with ether. The organic layer was washed with a saturated brine, dried over magnesium sulfate, and the solvent was removed by evaporation under reduced pressure to obtain an oily substance. Next, the thus obtained oily substance was dissolved in dry ether (10 ml), and the resulting solution was added at 0° C. to a suspension of lithium aluminum hydride (220 mg, 5.8 mmol) in dry ether (80 ml). The resulting mixture was stirred for 20 minutes and then a small amount of 2% aqueous sodium hydroxide solution was added thereto. After filtration of the reaction mixture through Celite, the solvent was removed by evaporation under reduced pressure, and the resulting oily substance was purified through silica gel column chromatography to give 1.5 g of alcohol X (yield: 46%). The compound obtained exhibited the physicochemical properties as shown below, from which it was identified to be the title compound.

$^1$H NMR (CDCl$_3$) δ ppm: 7.70–7.55 (m, 4H,) 7.46–7.30 (m, 6H,) 5.36–5.22 (m, 2H,) 4.75 (wide s, 1H,) 4.20 (wide s, 2H,) 3.92–3.35 (m, 6H,) 2.50–2.35 (m, 2H,) 1.90–1.15 (m, 11H) 1.04 (s, 9H,) 0.74–0.95 (m, 6H,).

$^{13}$C NMR (CDCl$_3$) δ ppm: 135.6, 133.8, 133.7, 131.1, 129.6, 127.6, 96.6, 96.5, 84.9, 66.3, 61.9, 61.5, 54.6, 46.2, 44.2, 35.1, 32.1, 30.3, 26.9, 25.4, 25.3, 21.5, 20.7, 20.6, 19.3, 19.1.

PREPARATION EXAMPLE 4

Preparation of 5R*-(t-butyldiphenylsiloxy)methyl-8S*-isopropyl-10-p-toluensulfonyloxy-6-decen-2-in-1-ol (Compound XI)

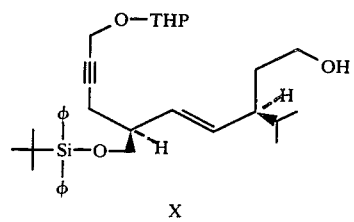

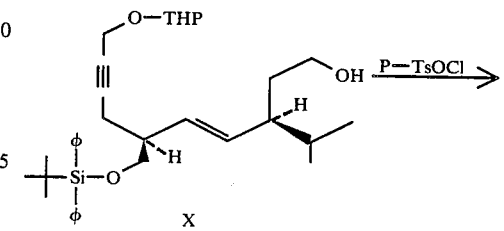

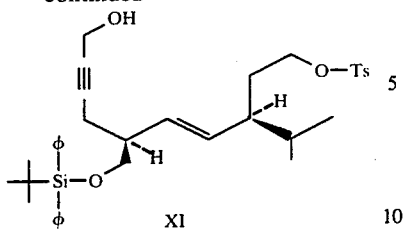

XI

To a solution of the alcohol X (4.5 g, 7.9 mmol) in pyridine (4 ml, 48 mmol) was added p-toluenesulfonyl chloride (4.5 g, 24 mmol) at 0° C. After stirring the solution at room temperature for 15 hours, the reaction solution was cooled and poured into an aqueous 3N-hydrochloric acid solution. After extraction with ether, the organic layer was washed with a saturated aqueous sodium bicarbonate solution, subsequently with a saturated brine and then dried over magnesium sulfate. The solvent was removed by evaporation under reduced pressure to obtain a tosylated compound as an oily substance. Next, the thus obtained compound was dissolved in methanol (40 ml) together with a catalytic amount of p-toluenesulfonic acid, followed by stirring at room temperature for 1 hour. The reaction mixture was poured into a saturated aqueous sodium bicarbonate solution, and then extracted with ether. The organic layer was washed with a saturated brine and dried over magnesium sulfate. The solvent was removed by evaporation under reduced pressure and the resulting oil was purified through silica gel column chromatography to give 4.3 g of alcohol XI (yield: 84%). The compound obtained exhibited the physicochemical properties as shown below, from which it was identified to be the title compound.

$^1$H NMR (CDCl$_3$) δ ppm: 7.80–7.54 (m, 6H,) 7.50–7.16 (m, 8H,) 5.25–5.10 (m, 2H,) 4.26–3.86 (m, 4H,) 3.60 (d, 2H, J=3.8 Hz,) 2.39(s, 3H,) 2.3–1.2(m, 5H) 1.04(s, 9H,) 0.83, 0.79(d, 6H, J=5.6 Hz,).

IR(neat); 3550, 3400, 2960, 2880, 1600, 1450, 1430, 1365, 1380, 1200, 1180, 1120, 980, 960, 920, 820, 750, 700, 670, 620, 560, 500 cm$^{-1}$.

$^{13}$C NMR(CDCl$_3$) δ ppm: 144.5, 135.6, 133.7, 133.5, 132.1, 132.0, 129.7, 127.8, 127.6, 84.4, 79.8, 69.4, 66.0, 51.3, 45.3, 44.0, 31.8, 31.4, 26.9, 21.5, 21.2, 20.4, 19.3, 18.8.

PREPARATION EXAMPLE 5

Preparation of
5R*-(t-butyldiphenylsiloxy)methyl-8S*-isopropyl
-10-p-toluenesulfonyloxy-(Z,E)-2,6-decadien-1-ol
(Compound XII)

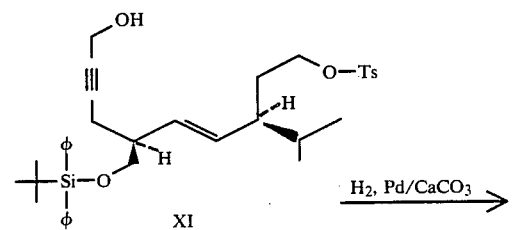

XI

H$_2$, Pd/CaCO$_3$ →

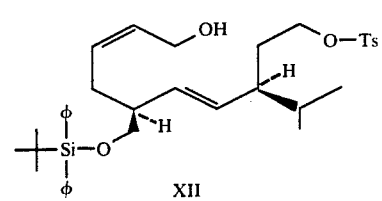

XII

The alcohol XI (1.57 g, 2.5 mmol) and 5% Pd/CaCO$_3$ (300 mg) was added to ethyl acetate (5 ml), and the resulting mixture was stirred under hydrogen atmosphere for 1 hour. After the reaction solution was filtered through florisil, the organic layer was removed by evaporation under reduced pressure to give 1.55 g of allylic alcohol XII (yield: 97%). The compound obtained exhibited the physicochemical properties as shown below, from which it was identified to be the title compound.

IR (neat); 3550, 3400, 2950, 2850, 1600, 1460, 1425, 1360, 1180, 1110, 970, 820, 760, 730, 700, 660 cm$^{-1}$.

$^1$H NMR (CDCl$_3$) δ ppm: 7.74–7.50(m, 6H,) 7.42–7.10(m, 8H,) 5.7–5.3(m, 2H,) 5.10–4.96(m, 2H,) 4.1(d, 2H, J=5.6 Hz,) 4.05–3.80(m, 2H,) 3.44(d, 2H, J=5.1 Hz,) 2.35(s, 3H,) 2.3–1.1(m, 7H) 1.04(s, 9H,) 0.78, 0.76(d, 7H, J=6.6 Hz,).

$^{13}$C NMR(CDCl$_3$) δ ppm: 144.5, 135.6, 133.8, 133.5, 133.0, 131.9, 130.6, 129.7, 127.8, 127.7, 69.4, 66.9, 58.6, 45.6, 45.3, 31.7, 31.4, 29.2, 21.5, 20.5, 19.3, 18.8.

PREPARATION EXAMPLE 6

Preparation of
6R*-(t-butyldiphenylsiloxy)methyl-2-(1-ethoxy)-9S*-
isopropyl-11-p-toluenesulfonyloxy-(Z,E)-3,7-
undecadienonitrile (Compound II')

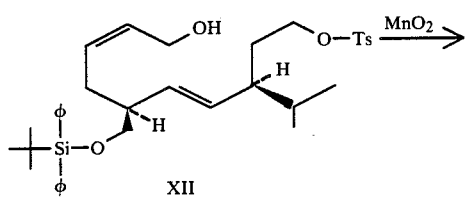

XII

MnO$_2$ →

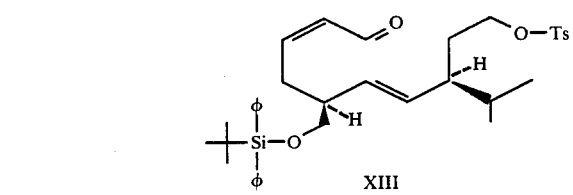

XIII

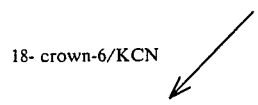

18- crown-6/KCN

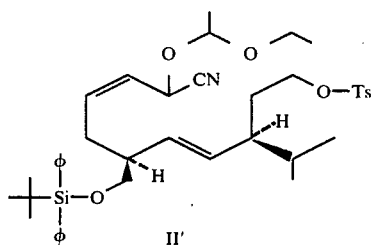

The allylic alcohol of Formula XII (2.6 g, 4.1 mmol) and manganese dioxide (3.5 g, 41 mmol) were stirred in ether (20 ml) at room temperature for 20 hours. The resulting suspension was filtered through florisil, and the filtrate was condensated under reduced pressure to obtain enal XIII as a crude product. The crude product was used without purification for the subsequent reaction. Namely, the enol XIII (2.6 g) and a catalytic amount of 18-crown-6/KCN were added to trimethylsilylcyanide (3 ml), and the resulting mixture was stirred at 0° C. for 15 minutes. Next, benzyltrimethylammonium fluoride (200 mg) was added to tetrahydrofuran (8 ml) and water (2 ml), and the resulting mixture was added at 0° C. to the reaction solution prepared above. After stirring the solution for 1 hour, the reaction mixture was poured into a saturated brine and extracted with ether. The organic layer was removed by evaporation under reduced pressure to obtain a cyanohydrin compound as a crude product. The thus obtained compound and a small amount of p-toluenesulfonic acid were dissolved in dry benzene (20 ml), and to the resulting solution ethyl vinyl ether (0.5 ml, 5.2 mmol) was added dropwise at 0° C. After stirring the resulting mixture for 20 minutes, a saturated aqueous sodium bicarbonate solution was added to the reaction mixture, followed by extraction with ether. The organic layer was washed with a saturated brine, dried over magnesium sulfate and concentrated under reduced pressure. The resulting yellow oil was purified through silica gel column chromatography to give 2.4 g of cyanhydrin ether II' (yield; 80%). The compound obtained exhibited the physicochemical properties as shown below, from which it was identified to be the title compound.

IR (neat); 2900, 1600, 1460, 1380, 1360, 1180, 1100, 810, 740, 700, 660, 610, 550, 500 cm$^{-1}$.

$^1$H NMR (CDCl$_3$) δ ppm: 7.8–7.5(m, 6H,) 7.5–7.1(m, 8H,) 5.7–4.6(m, 6H,) 4.1–3.3(m, 6H,) 2.36(s, 3H,) 1.04(s, 9H,) 2.4–1.0(m, 13H) 0.80, 0.74(d, 6H, J=6.7 Hz,).

EXAMPLE 1

Preparation of
8R*-isopropyl-5R*-(t-butyldiphenylsiloxy)-methyl-
(Z,E)-2,6-cyclodecadien-1-one

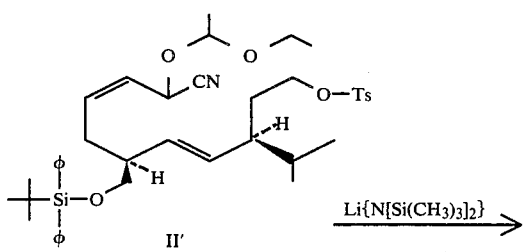

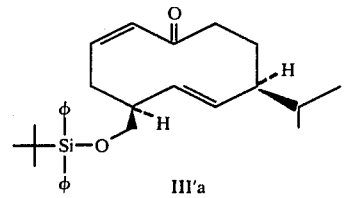

The cyanohydrin ether II' (2.6 g, 3.55 mmol) was dissolved in benzene (100 ml) and the resulting solution was added dropwise to a solution of lithiumbis(trimethylsilyl)amide (19.5 mmol) in benzene (100 ml) at 80° C. over 1 hour in a nitrogen stream. After stirring for further 30 minutes, the reaction mixture was cooled to room temperature and the reaction mixture was poured into a saturated aqueous ammonium chloride solution, followed by extraction with ether. The organic layer was washed with a saturated brine and dried over magnesium sulfate. The solvent was removed by evaporation under reduced pressure to give a brown oil. The oil and a catalytic amount of p-toluenesulfonic acid were poured into methanol (40 ml) and the resulting mixture was stirred at 0° C. for 1 hour. The reaction solution was extracted with ether and the organic layer was washed with a saturated brine, followed by drying over magnesium sulfate. The solvent was removed under reduced pressure and a brown oily substance was purified through silica gel column chromatography to give 1.04 g (yield) 69%) of 10-membered enone III'a, which is the desired compound. Results of identification are shown below.

IR (neat); 2900, 1685, 1620, 1460, 1430, 1380, 1360, 1110, 980, 820, 800, 740, 700, 610, 500 cm$^{-1}$.

$^1$H NMR (CDCl$_3$) δ ppm: 7.70–7.56(m, 4H,) 7.44–7.25(m, 6H,) 6.26(d, 1H, J=11.5 Hz,) 5.70(ddd, 1H, J=6.4, 9.0, 11.5 Hz,) 3.90–4.20(m, 2H,) 3.64(dd, 1H, J=5.5, 9.4 Hz,) 3.52(dd, 1H, J=7.3, 9.4 Hz,) 2.6–1.2(m, 9H) 1.04(s, 9H,) 0.84, 0.76(d, 6H, J−5.9 Hz,).

$^{13}$C NMR(CDCl$_3$) δ ppm: 206.9, 135.6, 135.2, 134.4, 133.8, 130.0, 129.6, 127.7, 66.4, 41.4, 31.5, 29.7, 29.4, 26.9, 20.9, 20.5, 19.3, 15.3.

TLC(ether/hexane=1/1) Rf=0.605.

EXAMPLE 2

Preparation of
8S*-isopropyl-5R*-(t-butyldiphenylsiloxy)methyl-
(2R*,3R*)-epoxy-6-cyclodecen-1-one

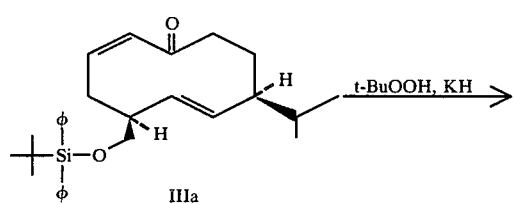

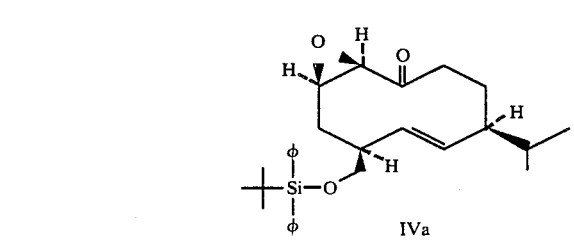

Potassium hydride (65 mg, 1.63 mmol) was suspended in tetrahydrofuran (8 ml) and to the suspension was added anhydrous t-butylhydroperoxide (0.52 ml, 1.63 mmol/3.15M-toluene solution) at −20° C. The mixture was stirred for 20 minutes, followed by dropwise addition of compound IIIa (110 mg, 0.23 mmol) thereto at −20° C. After 2 hours' stirring under the same condition, the solution was poured into cold water, followed by extraction with ether. The organic layer was washed with sodium thiosulfate, subsequently with a saturated brine and dried over magnesium sulfate. The solvent was removed by evaporation under reduced pressure and the residue was purified through silica gel column chromatography to give 81 mg of epoxide IVa (yield 80%).

IR (neat); 2950, 2850, 1715, 1590, 1460, 1430, 1380, 1360, 1240, 1110, 980, 940, 910, 820, 795, 735, 700, 680, 610, 500 cm$^{-1}$.

$^1$H NMR (CDCl$_3$) δ ppm: 7.70–7.56(m, 4H,) 7.44–7.25(m, 6H,) 5.45(dd, 1H, J=7.4, 15 Hz,) 4.92(dd, 1H, J=9.0, 15 Hz,) 3.66(d, 1H, J=4.8 Hz,) 3.65(dd, 1H, J=5.5, 9.4 Hz,) 3.60(dd, 1H, J=7.8, 9.4 Hz,) 3.24(ddd, 1H, J=2.6, 4.7, 10.2 Hz,) 2.65–1.1(m, 9H) 1.04(s, 9H,) 0.82, 0.7(d, 6H, J=7.7 Hz,).

$^{13}$C NMR (CDCl$_3$) δ ppm: 205.1, 136.3, 135.5, 133.6, 129.6, 129.3, 127.7, 66.9, 59.1, 58.4, 53.3, 40.1, 38.0, 31.6, 30.4, 27.6, 26.8, 20.7, 19.2.

TLC(ether/hexane=1/1) Rf=0.34.

EXAMPLE 3

Preparation of 8S*-isopropyl-5R*-hydroxymethyl-(2R*,3R*)-epoxy-6-cyclodecen-1-one

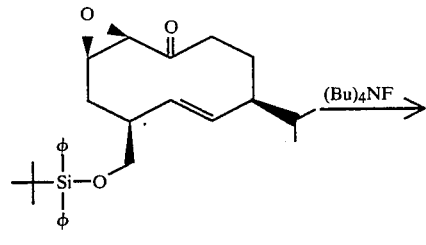

IV a

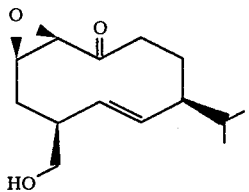

IV'

The epoxide IVa (78 mg, 0.17 mmol) was dissolved in tetrahydrofuran (2.0 ml) and to the resulting solution was added tetrabutylammonium fluoride (46 mg, 0.17 mmol). After the mixture was stirred at room temperature for 2 hours, the reaction solution was poured into a saturated brine, followed by extraction with ether. The organic layer was dried over magnesium sulfate and the solvent was removed by evaporation under reduced pressure. The residue was purified through silica gel column chromatography to give 31 mg of alcohol IV' (yield 79%).

mp 133°–135° C. (ethanol-hexane).

TLC(ether) Rf=0.29.

IR (neat); 3250, 2900, 2850, 1710, 1420, 1380, 1180, 1100, 1080, 1030, 1005, 975, 940, 800, 660 cm$^{-1}$.

$^1$H NMR (CDCl$_3$) δ ppm: 5.62(dd, 1H, J=7.7, 15.9 Hz,) 4.96(dd, 1H, J=8.7, 15.9 Hz,) 3.69(d, 1H, J=4.7 Hz,) 3.55(m, 2H,) 3.24(ddd, 1H, J=2.8, 4.7, 10.4 Hz,) 2.6–2.0(m, 4H) 1.0–2.0(m, 5H) 0.88, 0.80(d, 6H, J=6 Hz,).

$^{13}$C NMR(CDCl$_3$) δ ppm: 205.2, 136.7, 129.1, 66.1, 59.0, 58.0, 53.3, 40.1, 38.0, 31.6, 30.5, 27.6, 20.9, 20.7.

REFERENTIAL EXAMPLE 1

Preparation of diene compound VIV

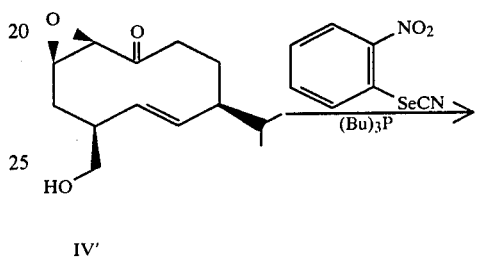

IV'

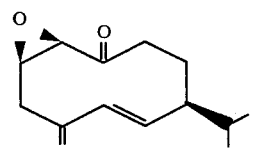

XIV

The alcohol IV' (36 mg, 0.15 mmol) and o-nitrophenylselenonitrile (103 mg, 0.45 mmol) were dissolved in tetrahydrofuran (3 ml). Then, to the resulting solution, tributylphosphine (0.112 ml, 0.45 mmol) was added, followed by stirring at room temperature for 30 minutes. Subsequently, 35% hydrogen peroxide (0.5 ml) was added to the mixture, followed by stirring at room temperature for 10 hours. The reaction solution was diluted with ether and the resulting mixture was poured into an aqueous sodium thiosulfate solution, followed by extraction with ether. The organic layer was washed with a saturated brine and dried over magnusium sulfate. The solvent was removed by evaporation under reduced pressure and the residue was purified through silica gel column chromatography to give 28 mg of diene XIV (85%). The compound obtained exhibited the physicochemical properties as follows.

mp 83.5°–86° C. (hexane).

TLC(ether/hexane=2/1) Rf=0.47.

IR(CHCl$_3$); 3000, 2950, 2850, 1715, 1610, 1440, 1415, 1380, 1325, 1250, 1120, 1060, 1020, 980, 800, 650 cm$^-$.

$^1$H NMR (CDCl$_3$) δ ppm: 5.90(d, 1H, J=15.9 Hz,) 5.07, 4.94(s, 2H,) 4.98(dd, 1H, J=8.9, 15.9 Hz,) 3.60(d, 1H, J=4.7 Hz,) 3.10(ddd, 1H, J=3.4, 4.7, 9.8 Hz,) 2.80(dd, 1H, J=3.4, 12.3 Hz,) 2.22(dd, 1H, J=9.8, 12.3 Hz,) 1.2–0.5 (m, 6H) 0.80, 0.88(d, 6H, J=6.4 Hz).

$^{13}$C NMR(CDCl$_3$) δ ppm: 204.9, 140.6, 137.6, 129.3, 115.7, 59.4, 59.1, 52.3, 39.7, 34.8, 31.9, 26.9, 20.1.

REFERENTIAL EXAMPLE 2

Preparation of hydroxyketone compound XV

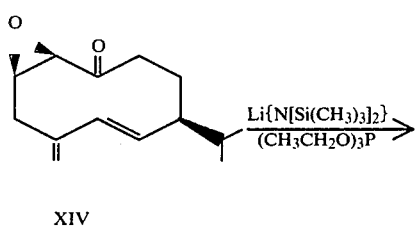

XIV

XV

The diene XIV (30 mg, 0.14 mmol) was dissolved in a mixture of hexamethyl phospholamide (0.7 ml) and tetrahydrofuran (0.5 ml), and the resulting solution was added dropwise to a solution of tetrahydrofuran (2 ml) containing lithium bis(trimethylsilyl)amide (0.55 mmol) at −78° C. in a nitrogen stream. Ten minutes later, triethylphosophite (0.25 ml) was added thereto and oxygen was charged thereinto at −78° C. for 2 hours. The reaction mixture was poured into an aqueous ammonium chloride solution, followed by extraction with ether. The organic layer was washed with a saturated brine and dried over magnesium sulfate. The solvent was removed by evaporation under reduced pressure and the residue was purified through silica gel column chromatography to give 17 mg of hydroxyketone XV (yield 51%). The compound thus obtained had the analytic values as follows.

mp 109.5° to 111.0° C. (recrystallized from ether-hexane).

TLC (ether/hexane=3/1) Rf=0.42.

HRMS Calculated value (for $C_{14}H_{20}O_3$) 236.1288, Found value 236.1413.

IR (CHCl$_3$); 3550, 2950, 2850, 1720, 1610, 1440, 1410, 1380, 1250, 980, 960, 900 cm$^{-1}$.

$^1$H NMR (CDCl$_3$) δ ppm: 5.92(d, 1H, J=15.9 Hz,) 5.11, 4.96(s, 2H,) 4.98(dd, 1H, J=10, 16 Hz,) 4.07(dd, 1H, J=1.7, 10 Hz,) 3.83(d, 1H, J=4.7 Hz,) 3.18(ddd, 1H, J=3.4, 4.7, 9.9 Hz,) 2.84(dd, 1H, J=3.4, 13 Hz,) 2.45-1.20(m, 5H) 0.91, 0.78(d, 6H, J=6.4 Hz,).

$^{13}$C NMR(CDCl$_3$) δ ppm: 20.4, 20.6, 31.6, 34.8, 35.7, 48.6, 58.1, 59.9, 73.3, 116.4, 128.9, 138.0, 140.1, 204.2

REFERENTIAL EXAMPLE 3

Preparation of diketone compound XVI

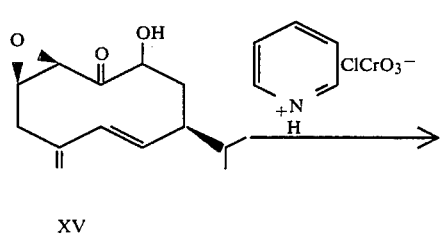

XV

XVI

The hydroxyketone XV (15 mg, 0.064 mmol) was dissolved in dichloromethane (0.5 ml). To the resulting solution, was added pyridinium chlorochromate (PCC 50 mg) at room temperature, followed by stirring for 6 hours. After the reaction mixture was filtered through a florisil, the filtrate was concentrated and the residue was purified through silica gel column chromatography to give 11 mg of diketon XVI (yield 76%).

TLC (ether/hexane=1/1) Rf=0.60.

HRMS Calculated (for $C_{14}H_{18}O_3$) 234.1256, Found 234.1286.

IR (neat); 2950, 2850, 1700, 1610, 1440, 1405, 1380, 1360, 1300, 1240, 1070, 1000, 960, 980, 920, 900, 840, 750, 720, 600 cm$^{-1}$.

$^1$H NMR (CDCl$_3$) δ ppm: 5.90(d, 1H, J=16.5 Hz,) 5.25(dd, 1H, J=10, 3, 16.5 Hz,) 5.16, 4.99(s, 2H,) 4.40(d, 1H, J=5.0 Hz,) 3.50(dd, 1H, J=10.3, 11.1 Hz,) 3.22(ddd, 1H, J=3.4, 4.8, 9.8 Hz,) 2.90(dd, 1H, J=3.4, 12.8 Hz,) 2.40(dd, 1H, J=5.4, 10.3 Hz,) 2.30-1.85(m, 1H,) 2.10(dd, 1H, J=9.8, 13 Hz,) 1.8-1.5(m, 1H,) 0.95, 0.88(d, 6H,).

$^{13}$C NMR(CDCl$_3$) δ ppm: 19.9, 20.0, 32.4, 34.9, 40.0, 49.5, 55.2, 59.4, 117.4, 130.5, 135.8, 139.3, 193.5, 201.8.

REFERENTIAL EXAMPLE 4

Preparation of (±) periplanone-B (compound XVII)

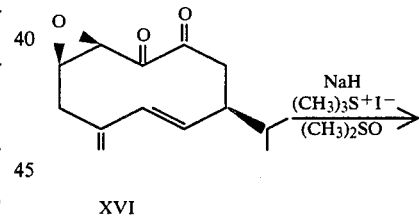

XVI

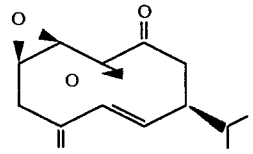

XVII (±) periplanone-B

Sodium hydride (1 mg, 0.04 mmol) was added to dimethylsulfoxide (0.5 ml) and the mixture was stirred at 40° C. for 30 minutes. To the resulting solution was added tetrahydrofuran (0.5 ml), followed by cooling to −5° C. To the reaction mixture was added trimethylsulfonium iodide (8.2 mg, 0.04 mmol)/dimethylsulfoxide (0.4 ml) at −5° C. This mixture was gradually added to a mixed solution of the diketone XVI (9.4 mg, 0.04 mmol) and tetrahydrofuran (1 ml) at 0° C. in nitrogen stream. The reaction mixture was poured into a saturated ammonium chloride solution, followed by extraction with ether. The organic layer was washed with a saturated brine and dried over magnesium sulfate. The solvent was removed by evaporation under reduced pressure and the residue was purified through silica gel column chromatography to give 5.7 mg of (±) periplanone-B XVII as a colorless oily substance (yield 57%). The analytical values of the compound thus obtained were as follows.

TLC (ether/hexane=1/1) Rf=0.53.

IR (neat): 3070, 2950, 2860, 1705, 1605, 1450, 1380, 1360, 1330, 1305, 1270, 1250, 1120, 1020, 975, 910, 860, 840, 750, 720, 580 cm$^{-1}$.

$^1$H NMR (CDCl$_3$, 200 MHz) δ ppm: 6.04(d, 1H, J=16.1 Hz) 5.89(dd, 1H, J=9.5, 16.1 Hz) 5.10, 4.97(s, 2H) 3.81(d, 1H, J=3.9 Hz) 3.03, 2.83(d, 2H, J=5.6 Hz) 2.94(ddd, 1H, J=3.9, 4.3, 10 Hz) 2.80–2.62(m, 2H) 2.68(dd, 1H, J=11.0, 11.4 Hz) 2.20(dd, 1H, J=5.6, 11.4 Hz) 2.23–2.12(m, 1H,) 1.7–1.5(m, 1H,) 0.883, 0.915(d, 1H, J=6.3 Hz).

HRMS Calculated (for C$_{15}$H$_{20}$O$_3$) 248.1413 Found 248.1402.

According to the present invention, the compound represented by Formula II may be cyclized in extremely high yield (69% or more) by the intramolecular alkylation to provide a compound of Formula III. Also, if desired, the double bond at α- and β-positions relative to the carbonyl group in Compound III can be epoxidized site-specifically and stereo-specifically with a selectivity of 95% or more, thereby to provide a compound of Formula IV, which constitutes, together with the compound of Formula III, a group of compounds represented by a common Formula I.

Further, in the case whee the present invention is applied to the total synthesis of periplanone-B which is a sex pheromone of periplaneta, the desired product may be obtained easily and in a high yield starting from inexpensive materials.

We claim:

1. A compound of Formula I:

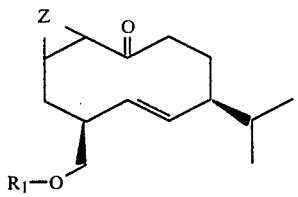

wherein R$_1$ represents a hydrogen atom or a protective group for a hydroxyl group; and Z represents a direct bond (2,3-cis-5R*,8S*) or an oxygen atom which forms an oxirane ring having a configuration of (2R*, 3R*, 5R*, 8S*).

2. The compound according to claim 1, wherein R$_1$ in Formula I represents one selected from the group consisting of a hydrogen atom, a

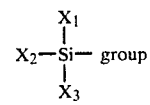

wherein X$_1$, X$_2$ and X$_3$ may be the same or different and each represent a lower alkyl group, an arylalkyl group or an aryl group, a tetrahydropyranyl group, a tetrahydrothiopyranyl group, a benzyloxymethyl group, an ethoxyethyl group and a methoxymethyl group.

3. The compound according to claim 1, 8-isopropyl-5-(t-butyldiphenylsiloxy)methyl -2,6-cyclodecadien-1-one.

4. The compound according to claim 1, 8-isopropyl-5-(dimethyl-t-butylsiloxy)methyl-2,6-cyclodecadien-1-one.

5. The compound according to claim 1, 8-isopropyl-5-(triphenylsiloxy)methyl-2,6-cyclodecadien-1-one.

6. The compound according to claim 1, 8-isopropyl-5-(t-butyldiphenylsiloxy)methyl-2,3-epoxy-6-cyclodecen-1-one.

7. The compound according to claim 1, 8-isopropyl-5-(dimethyl-t-butylsiloxy)methyl-2,3-epoxy-6-cyclodecen-1-one.

8. The compound according to claim 1, 8-isopropyl-5-(triphenylsiloxy)methyl-2,3-epoxy-6-cyclodecen-1-one.

* * * * *